United States Patent [19]

Dragoo

[11] Patent Number: 4,795,454

[45] Date of Patent: Jan. 3, 1989

[54] ABSORBENT ARTICLE HAVING LEAKAGE-RESISTANT DUAL CUFFS

[75] Inventor: Jerry L. Dragoo, Fairfield, Ohio

[73] Assignee: The Procter & Gamble Company, Cincinnati, Ohio

[21] Appl. No.: 117,379

[22] Filed: Oct. 30, 1987

Related U.S. Application Data

[63] Continuation of Ser. No. 917,450, Oct. 10, 1986, abandoned.

[51] Int. Cl.[4] .............................................. A61F 13/16
[52] U.S. Cl. .................................. 604/385.2; 604/378
[58] Field of Search .................... 604/378, 385.1, 385.2, 604/381, 382, 389

[56] References Cited

U.S. PATENT DOCUMENTS

| | | |
|---|---|---|
| 2,545,674 | 3/1951 | Ralph .................................. 604/397 |
| 2,575,164 | 11/1951 | Donovan . |
| 2,916,037 | 12/1959 | Hansen . |
| 3,386,442 | 6/1968 | Sabee . |
| 3,452,753 | 7/1969 | Sanford . |
| 3,530,859 | 9/1970 | Helmowitz . |
| 3,572,342 | 3/1971 | Lindquist . |
| 3,593,716 | 7/1971 | Vogt . |
| 3,658,064 | 4/1972 | Pociluyko . |
| 3,665,920 | 9/1972 | Davis . |
| 3,667,466 | 6/1972 | Ralph . |
| 3,744,494 | 7/1973 | Marsan . |
| 3,771,524 | 11/1973 | Ralph . |
| 3,807,402 | 4/1974 | Miller . |
| 3,825,006 | 7/1974 | Ralph . |
| 3,828,784 | 8/1974 | Zoephel ........................ 604/385.2 |
| 3,860,003 | 1/1975 | Buell . |
| 3,920,017 | 11/1975 | Karami . |
| 3,929,134 | 12/1975 | Karami . |
| 3,930,501 | 1/1976 | Schaar . |
| 3,978,861 | 9/1976 | Schaar . |
| 3,995,640 | 12/1976 | Schaar . |
| 3,999,547 | 12/1976 | Hernandez ........................ 604/370 |
| 4,040,423 | 8/1977 | Jones, Sr. ........................ 604/378 |
| 4,041,950 | 8/1977 | Jones, Sr. ........................ 604/385 R |
| 4,090,515 | 5/1978 | Karami . |
| 4,210,143 | 7/1980 | De Jonckheere ................ 604/370 |
| 4,326,528 | 4/1982 | Ryan et al. . |
| 4,413,996 | 11/1983 | Taylor . |
| 4,490,148 | 12/1984 | Beckestrom ........................ 604/385 |
| 4,500,316 | 2/1985 | Damico ........................ 604/389 |
| 4,589,876 | 5/1986 | Van Tillburg . |
| 4,636,207 | 1/1987 | Buell . |
| 4,657,539 | 4/1987 | Hasse . |
| 4,662,877 | 5/1987 | Williams ........................ 604/385 A |
| 4,681,579 | 7/1987 | Toussant et al. . |
| 4,687,478 | 8/1987 | Van Tillburg . |
| 4,695,278 | 9/1987 | Lawson . |
| 4,704,115 | 11/1987 | Buell . |
| 4,704,116 | 11/1987 | Enloe . |

FOREIGN PATENT DOCUMENTS

| | | |
|---|---|---|
| 45217 | 2/1986 | Australia . |
| 0070584 | 1/1983 | European Pat. Off. . |
| 2561078A1 | 2/1984 | France . |
| 41-18031 | 8/1966 | Japan . |
| 2159693 | 12/1985 | United Kingdom . |
| 2161059 | 1/1986 | United Kingdom ............ 604/385 R |
| 2193625A | 2/1988 | United Kingdom . |

Primary Examiner—C. Fred Rosenbaum
Assistant Examiner—Denise Whelton
Attorney, Agent, or Firm—Steven W. Miller; John M. Pollaro; Fredrick H. Braun

[57] ABSTRACT

An integral disposable absorbent article such as a diaper provided with an absorbent core, a liquid impervious backsheet, an elastically contractible gasketing cuff preferably formed by a gasketing flap and a flap elastic member, a barrier cuff having a flap portion and a channel portion comprising a proximal edge and a distal edge, and a liquid pervious topsheet. The topsheet extends outwardly toward the edge of the absorbent core and terminates inwardly of the proximal edge. A seal means for adjoining the proximal edge to the gasketing flap is positioned along the proximal edge so as to provide a leakage-resistant seal along the proximal edge. The barrier cuffs may be provided with spacing means for spacing the distal edges away from the liquid-receiving surface so as to enhance the containment characteristics of the barrier cuffs. Thus, body exudates which wick through and along the topsheet are prevented from flowing to the edges of the diaper and underneath the barrier cuffs because of the seal formed along the proximal edges and because the topsheet terminates inwardly of the proximal edges.

21 Claims, 1 Drawing Sheet

ABSORBENT ARTICLE HAVING LEAKAGE-RESISTANT DUAL CUFFS

This is a continuation of application Ser. No. 917,450, filed Oct. 10, 1986, now abandoned.

FIELD OF THE INVENTION

The present invention relates to absorbent articles such as disposable diapers, and more particularly, to absorbent articles having a gasketing cuff and a barrier cuff which improve the containment characteristics of the absorbent article.

BACKGROUND OF THE INVENTION

The major function of absorbent articles such as disposable diapers and adult incontinent briefs is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist to adjacent clothing because they are not immediately absorbed within the article. For example, urine tends to wick through the topsheet to the edges of the absorbent article where it can come in contact with clothing or other articles. Additionally, loose fecal material that is not easily absorbed by the absorbent article tends to "float" on the liquid-receiving surface and work its way past the legs or waist of the wearer.

Contemporary disposable diapers have a topsheet, a backsheet, an absorbent core, and elasticized leg flaps generally formed from an elastic member being enclosed in the continuous topsheet and backsheet which extend beyond the edges of the absorbent core. These elasticized leg flaps prove effective generally to prevent wicking and overflow from the fluid laden diaper to clothing contacting the edges of the diaper in that the elasticized leg flaps present a fluid impervious barrier between the edge of the diaper and the contacting clothing, and in addition, provide a gasketing action about the legs of the wearer. However, leakage along the perimeter of the diaper may still occur. As liquids are discharged onto the topsheet, some of the liquid flows on the surface of the topsheet and some of the liquid is absorbed by and wicks through the topsheet. As the liquid migrates toward the edges of the diaper, it may come in contact with clothing or undergarments where it can be absorbed by and wicked into such garments.

Disposable diapers may be provided with barrier cuffs which inhibit loose fecal material or gushes of urine or liquids from soiling the wearer's clothing. The barrier cuffs restrain the free flow of this material and provide a structure to hold such material within the diaper so that as such material freely floats or flows on the topsheet of the diaper, it is contained within the diaper. Despite the effectiveness of such structures in containing such material, it has been found that liquid can wick underneath and beyond the barrier cuffs and thus beyond the elasticized leg flaps and soil the wearer's clothing because the diaper construction does not present a barrier to the wicking of liquid through the topsheet.

Therefore, it is an object of the present invention to provide an absorbent article which has improved liquid containment characteristics.

It is an additional object of the present invention to provide an absorbent article having a barrier cuff which acts as a restraint against the leakage of body exudates.

It is a further object of the present invention to provide an absorbent article having an elastically contractible gasketing cuff and a barrier cuff so as to provide a dual rsetraint against the leakage of body exudates, thereby improving the containment characteristics of the absorbent article, especially in regard to loose fecal material.

It is also an object of the present invention to provide an absorbent article having a barrier cuff that is raised above the liquid-receiving surface of the article when the article is fitted on the wearer such that a channel is formed which restrains and holds body exudates within the article.

It is a still further object of the present invention to present a barrier to the wicking of liquids through the topsheet of the edges of the absorbent article, especially underneath the barrier cuffs, so as to enhance the containment characteristics of the absorbent article.

These and other objects of the invention will be more readily apparent when considered and referenced to the following description and when taken in connection with the accompanying drawings.

SUMMARY OF THE INVENTION

In accordance with the present invention, an integral disposable absorbent article such as a diaper is provided with an absorbent core having a garment surface and a body surface, a liquid impervious backsheet positioned adjacent the garment surface of the absorbent core, an elastically contractible gasketing cuff preferably formed by a gasketing flap extending outwardly from and along an edge of the absorbent core and a flap elastic member operatively associated with the gasketing flap in an elastically contractible condition, a barrier cuff having a flap portion and a channel portion comprising a proximal edge and a distal edge, and a liquid pervious topsheet positioned adjacent the body surface of the absorbent core. The topsheet extends outwardly toward the edge of the absorbent core and terminates inwardly of the proximal edge. A seal means for adjoining the proximal edge to the gasketing flap is positioned along the proximal edge so as to provide a leakage-resistant seal along the proximal edge. The barrier cuffs may be provided with spacing means for spacing the distal edges away from the liquid-receiving surface so as to enhance the containment characteristics of the barrier cuffs. In addition, closing means secure the end portions of the barrier cuffs closed to provide a more comfortable fit for the wearer and to obviate inversion of the barrier cuffs.

Leakage prevention is enhanced because the topsheet is not coterminous with the backsheet, and because the barrier cuff along with the backsheet defines the gasketing flap of the absorbent article. Thus, body exudates which wick through and along the topsheet contact the barrier cuff and are contained and held within the diaper so that they do not leak out of the diaper at the gaps between the diaper and the legs or waist of the wearer. Such exudates are prevented from flowing to the edges of the diaper and underneath the barrier cuffs because of the seal formed along the edges of the diaper and along the proximal edge by the seal means, the barrier cuff, and the backsheet, and because the topsheet preferably terminates inwardly of the proximal edge.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAIL DESCRIPTION OF THE INVENTION

Figure 1:
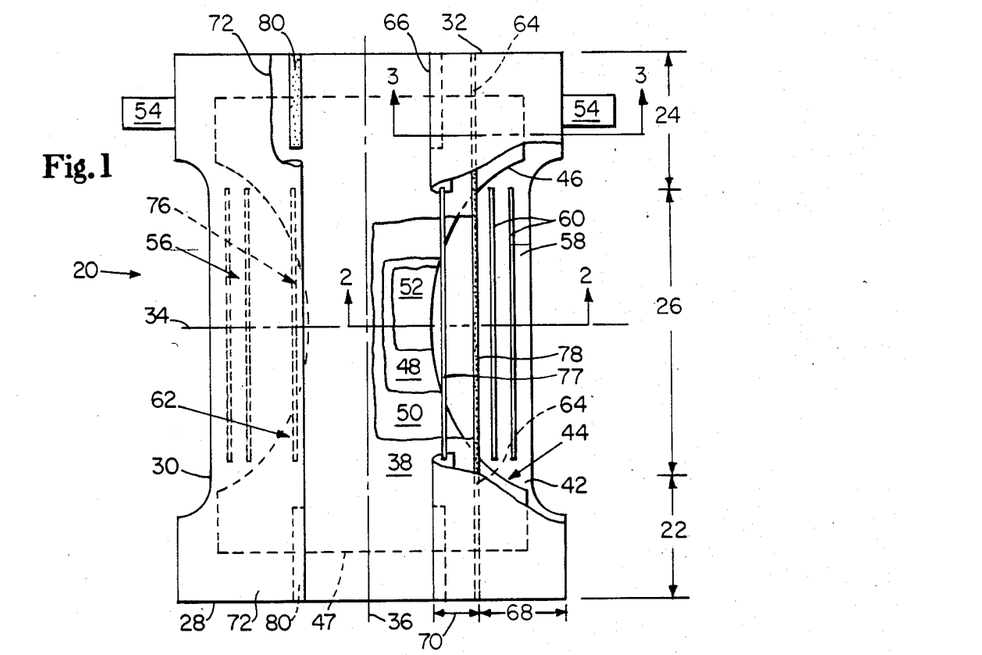
FIG. 1 is a plan view of a disposable diaper embodiment of the present invention having portions cut-away to reveal underlying structure.

As used herein, the term "integral disposable absorbent article" refers to articles which absorb and contain body exudates and more specifically refers to articles which are placed against or in proximity to the body of the wearer to absorb and contain the various exudates discharged from the body, which are intended to be discarded after a single use (i.e., they are not intended to be laundered or otherwise restored or reused), and which are unitary in that they do not require separate manipulative parts like a separate holder and liner. A preferred embodiment of the integral disposable absorbent article of the present invention, diaper 20, is shown in FIG. 1. As used herein, the term "diaper" refers to a garment generally worn by infants and incontinent persons that is worn about the lower torso of the wearer. It should be understood, however, that the present invention is also applicable to other integral disposable absorbent articles such as incontinent briefs and the like.

FIG. 1 is a plan view of the diaper 20 of the present invention in its flat-out, uncontracted state (i.e., with all elastic induced contraction pulled out) with portions of the structure being cut-away to more clearly show the construction of the diaper 20 and with the portion of the diaper 20 which contacts the wearer facing the viewer. The diaper 20 is shown in FIG. 1 to have a front waist region 22, a back waist region 24, a crotch region 26 and a periphery 28 which is defined by the outer edges of the diaper 20 in which the longitudinal edges are designated 30 and the end edges are designated 32. The diaper 20 additionally has a lateral centerline which is designated 34 and a longitudinal center line which is designated 36.

The diaper 20 comprises a liquid pervious topsheet 38, the liquid-receiving surface of the diaper 20 being generally defined by the topsheet 38 and being designated 40; a liquid impervious backsheet 42; an absorbent core 44 having a garment surface 85, a body surface 86, and edges that are designated side edges 46 and waist edges 47 and comprising an absorbent layer 48 and first and second tissue layers 50 and 52, respectively; a pair of tape-tab fasteners 54; gasketing cuffs 56 each comprising a gasketing flap 58 and one or more flap elastic members 60; barrier cuffs 62 each having a flap portion 68, a channel portion 70 comprising a proximal edge 64 and a distal edge 66, and ends 72; spacing means 76 such as a spacing elastic member 77 for spacing the distal edge 66 away from the liquid-receiving surface 40; and seal means 78 such as an adhesive bead for adjoining the proximal edge 64 to the gasketing flaps 58. The diaper 20 additionally comprises closing means 80 such as an adhesive bead for securing closed the ends 72 of each of the barrier cuffs 62.

FIG. 1 shows a preferred embodiment of the diaper 20 in which the backsheet 42 has length and width dimensions generally larger than those of the absorbent core 44. The backsheet 42 extends beyond the edges of the absorbent core 44 to thereby form the periphery 28 of the diaper 20. The periphery 28 defines the outer perimeter or, in other words, the edges of the diaper 20. The periphery 28 comprises the longitudinal edges 30 and the end edges 32. As shown in FIG. 1, the topsheet 38 is not coterminous with the backsheet 42 along at least the longitudinal edges 30 but is preferably associated with and superposed on the backsheet 42 adjacent the end edges 32.

The diaper 20 has front and back waist regions 22 and 24 extending, respectively, from the end edges 32 of the diaper periphery 28 toward the lateral centerline 34 of the diaper 20 a distance from about ¼ to about ⅓ the length of the diaper 20. The waist regions comprise those portions of the diaper 20 which, when worn, encircle the waist of the wearer. The crotch region 26 is that portion of the diaper 20 between the waist regions 22 and 24, and comprises that portion of the diaper 20 which, when worn, is positioned between the legs of the wearer and covers the lower torso of the wearer.

Figure 2:
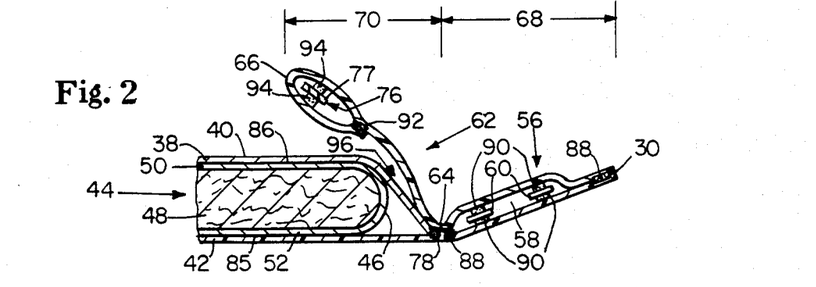
FIG. 2 is a fragmentary sectional view taken along section line 2—2 of FIG. 1.

FIG. 2 is fragmentary sectional view taken along line 2—2 of FIG. 1 and depicts a preferred diaper construction in the crotch region 26 of the diaper 20. The absorbent core 44 comprises the absorbent layer 48 that is shown as being completelt enveloped by the first and second tissue layers 50 and 52 which define the garment surface 85 and the body surface 86. The absorbent core 44 is disposed between the topsheet 38 and the backsheet 42; the backsheet 42 extending beyond the side edge 46 of the absorbent core 44. The flap portion 68 of the barrier cuff 62 is formed by affixing portions of a separate barrier cuff member to the backsheet 42 adjacent the longitudinal edge 30 of the diaper 20 with attachment means 88 such as an adhesive; a leakage-resistant seal being formed by the attachment means 88, the flap portion 68 and the backsheet 42 to provide protection against leakage of liquids wicking along the topsheet 38. The flap portion 68 of the barrier cuff 62 and the backsheet 42 define the gasketing flap 58 and enclose the flap elastic members 60 adjacent the longitudinal edge 30. The flap elastic members 60 are secured in the barrier cuff-backsheet formed gasketing flap 58 by flap elastic attachment means 90. The elastically contractible gasketing cuff 56 is thereby formed by the gasketing flap 58 and the flap elastic member 60. The channel portion 70 of the barrier cuff 62 is contiguous with the flap portion 68 and comprises the proximal edge 64 and the distal edge 66. The proximal edge 64 of the barrier cuff 62 is formed inboard of the gasketing cuff 56, preferably between the side edge 46 of the absorbent core 44 and the flap elastic members 60, by adjoining a segment of the barrier cuff member to the backsheet 42 by the seal means 78 such as an adhesive bead so as to form a leakage-resistant seal along the proximal edge 64 to present a barrier to liquid wicking through the topsheet 38 so as to prevent the liquids from wicking underneath the barrier cuffs to the edges of the diaper 20. The distal edge 66 is disposed inboard of the proximal edge 64 and is not secured to any underlying elements of the diaper 20. As shown in FIG. 2, the distal edge 66 is formed by folding the end of the barrier cuff member back upon itself and securing it to another segment of the barrier cuff member by the distal attachment means 92 to form a tunnel. A spacing means 76 such as a spacing elastic member 77 is enclosed in the tunnel that is formed when the end of the barrier cuff member is folded back upon itself; the spacing elastic member 77 being secured in the barrier cuff 62 by the spacing elastic attachment means 94. The distal edge 66 is thus spaced away from the liquid-receiving surface 40 by the elastic gathering action of the spacing elastic member 77; a channel 96 thereby being formed by at least the proximal edge 64 and the distal edge 66. The channel 96 is shown as being open and ready to restrain, contain, and hold body exudates until the diaper 20 is removed from the wearer. The topsheet 38 is positioned adjacent the body surface 86 of the absorbent core 44 and extends beyond the side edge 46 of the absorbent core 44 and terminates inwardly and preferably adjacent the proximal edge 64, where it is preferably secured with the gasketing flap 58 (backsheet 42) and the proximal edge 64 by the seal means 78 to provide a leakage-resistant seal along the proximal edge 64.

Figure 3:
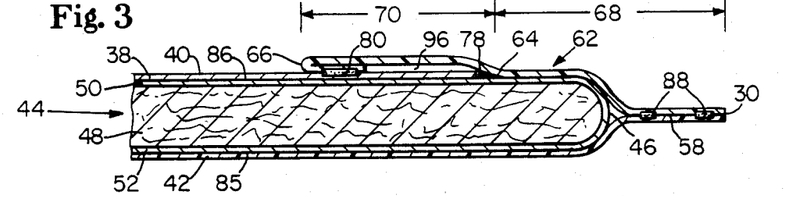
FIG. 3 is a fragmentary sectional view taken along section line 3—3 of FIG. 1.

FIG. 3 is a fragmentary sectional view taken along line 3—3 of FIG. 1 and depicts a preferred diaper construction in the back waist region 24 of the diaper 20. The absorbent core 44 comprises the absorbent layer 48 that is shown as being completely enveloped by the first and second tissue layers 50 and 52 which define the garment surface 85 and the body surface 86. The backsheet 42 extends beyond the side edge 46 of the absorbent core 44. The flap portion 68 of the barrier cuff 62 is formed by affixing portions of a separate barrier cuff member to the backsheet 42 adjacent the longitudinal edge 30 of the diaper 20 with an attachment means 88 such as an adhesive; a leakage-resistant seal being formed by the attachment means 88, the flap portion 68 and the backsheet 42 to provide protection against leakage of liquids emanating from the edges of the absorbent core 44 or wicking past the seal along the proximal edge 64. The flap portion 68 of the barrier cuff 62 and the backsheet 42 define the gasketing flap 58. A gasketing cuff 56 is not preferably disposed in the waist regions such that the flap elastic members 60 do not extend into this portion of the gasketing flap 58 and are not shown in FIG. 3. The channel portion 70 of the barrier cuff 62 is contiguous with the flap portion 68 and comprises the proximal edge 64 and the distal edge 66. The proximal edge 64 is formed by securing a segment of the barrier cuff member to the underlying structure (tissue layer 50) of the diaper 20 by the seal means 78 such as an adhesive bead. The topsheet 38 covers a portion of the body surface 86 of the absorbent core 44 and terminates inwardly of and preferably adjacent the proximal edge 64 where it is preferably secured with the proximal edge 64 by the seal means 78 to provide a leakage-resistant seal along the proximal edge 64. The distal edge 66 is secured inboard of the proximal edge 64 to the underlying structure (topsheet 38) of the diaper 20 by the closing means 80 such as an adhesive bead. Therefore, the distal edge 66 is closed (i.e., it is not open nor capable of being spaced away from the liquid-receiving surface 40) such that inversion of the barrier cuffs is prevented. It should also be noted that a spacing means 76 such as a spacing elastic member 77 is not disposed in this region because the distal edge 66 is preferably secured closed and is not designed to be spaced away from the liquid receiving surface 40 in the waist regions. Although the channel 96 is not open to restrain the flow of body exudates in the waist regions, it may act to contain and hold exudates which flow along the channel 96.

The absorbent core 44 may be any means which is generally compressible, conformable, non-irritating to the wearer's skin, and capable of absorbing and retaining liquids and certain body exudates. A preferred absorbent core 44 has a garment surface 85 and a body surface 86 and comprises an absorbent layer 48 and first and second tissue layers 50 and 52, respectively. The first and second tissue layers 50 and 52 overlay the major surfaces of the absorbent layer 48 to form the garment surface 85 and the body surface 86.

The absorbent layer 48 may be manufactured in a wide variety of sizes and shapes (e.g., rectangular, hourglass, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, super absorbent polymers, absorbent gelling materials, or any equivalent materials or combination of materials. The total absorbent capacity of the absorbent layer 48 should, however, be compatible with the design exudate loading in the intended use of the diaper 20. Further, the size and absorbent capacity of the absorbent layer 48 may be varied to accommodate wearers ranging from infants through adults.

A preferred embodiment of the diaper 20 shown in FIG. 1 has an hourglass-shaped absorbent layer 48 and is intended to be worn by infants ranging in weight from about 5 kgs to about 12 kgs (about 12 pounds to about 26 pounds). The airfelt used in the absorbent layer 48 weighs from about 30 grams to about 56 grams, has a generally uniform caliper, and has an absorbent capacity of from about 8 grams to about 16 grams of water per gram of absorbent material. It should be understood, however, that the size, shape, configuration, and total absorbent capacity of the absorbent layer 48 may be varied to accommodate wearers ranging from infants through adults. Therefore, the dimensions, shape, and configuration of the absorbent layer 48 may be varied (e.g., the absorbent layer may have a varying caliper, or a hydrophillic gradient, or may contain absorbent gelling materials). The absorbent layer 48 is preferably a batt of airfelt about 32 cm wide (lateral dimension), about 45 cm long (longitudinal dimension) and approximately 7 cm across the narrowest part of the crotch region.

The first and second tissue layers 50 and 52 improve the tensile strength of the absorbent core 44 and reduce the tendency of the absorbent layer 48 to split, lump or ball when wetted. The first and second tissue layer 50 and 52 also help to improve lateral wicking of the absorbed exudates, thereby providing a more even distribution of the exudates throughout the absorbent layer 48. While a number of materials and manufacturing techniques may be used to manufacture the first and second tissue layers 50 and 52, satisfactory results have been obtained with sheets of tissue paper having a basis weight of about 16 grams per square meter (10 lbs. per 3000 square feet) and having an air permeability of about 30.5 cubic meters per minute per square meter (100 cubic feet per minute per square foot) at a pressure differential of about 12.8 millimeters of water ($\frac{1}{2}$ inch). While the first and second tissue layers 50 and 52 are preferably coterminous with the absorbent layer 48, they may have different dimensions, a different configuration, or they may be omitted entirely.

The backsheet 42 is positioned adjacent the garment surface 85 of the absorbent core 44 and is preferably attached thereto by attachments means (not shown) such as those well known in the art. For example, the backsheet 42 may be secured to the absorbent core 44 by a uniform continuous layer of adhesive, a patterned layer of adhesive, or an array of separate lines or spots of adhesive. Adhesives which have been found to be satisfactory are manufactured by Eastman Chemical Products Company of Kingsport, Tennessee and marketed under the tradename Eastobond A-3 and Century Adhesives, Inc. of Columbus, Ohio and marketed under the tradename Century 5227.

The backsheet 42 is impervious to liquid and is preferably manufactured from a thin plastic film, although other flexible liquid impervious materials may also be used. The backsheet 42 prevents the exudates absorbed and contained in the absorbent core 44 from wetting articles which contact the diaper 20 such as bedsheets and undergarments. Preferably, the backsheet 42 is a polyethylene film having a thickness of from about 0.012 mm (0.5 mil) to about 0.051 cm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 42 is preferably embossed and/or matte finished to provide a more clothlike appearance. Further, the backsheet 42 may permit vapors to escape from the absorbent core 44 while still preventing exudates from passing through the backsheet 42.

The size of the backsheet 42 is dictated by the size of absorbent core 44 and the exact diaper design selected. In a preferred embodiment, the backsheet 42 has a modified hourglass shape extending beyond the absorbent core 44 a minimum distance of at least about 1.3 cm to about 2.5 cm (about 0.5 to about 1.0 inch) around the entire diaper periphery 28.

Tape tab fasteners 54 are typically applied to the back waist region 24 of the diaper 20 to provide a fastening means to hold the diaper on the wearer. The tape tab fasteners 54 can be any of those well known in the art, such as the fastening tape disclosed in U.S. Pat. No. 3,848,594 issued to K. B. Buell on Nov. 19, 1974, which is incorporated herein by reference. These tape tab fasteners 54 or other diaper fastening means, such as pins, are typically applied near the end edges of a diaper in its "in-use" configuration.

The topsheet 38 is compliant, soft feeling, and non-irritating to the wearer's skin. Further, the topsheet 38 is liquid pervious permitting liquids to readily penetrate through its thickness. A suitable topsheet may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from liquids in the absorbent core 44.

A preferred topsheet 38 comprises staple length polypropylene fibers having a denier of about 1.5, such as Hercules Type 151 polypropylene marketed by Hercules, Inc. of Wilmington, Del. As used herein, the term "staple length fibers" refers to those fibers having a length of at least about 15.9 mm (0.625 inches).

There are a number of manufacturing techniques which may be used to manufacture the topsheet 38. For example, the topsheet 38 may be woven, non-woven, spunbonded, carded, or the like. A preferred topsheet 38 is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross machine direction.

The topsheet 38 is substantially noncoterminous with the backsheet 42 along those edges of the diaper 20 in which a barrier cuff 62 is disposed so that liquids will not wick through the topsheet 38 to the edges of the diaper 20, preferably so that liquids will not wick underneath and beyond the proximal edges 64 of the barrier cuffs 62, thereby reducing the leakage of liquids out of the diaper 20. The topsheet 38 is positioned adjacent the body surface 86 of the absorbent core 44 and overlays a major portion of the absorbent core 44 so that exudates are discharged onto the topsheet 38 and penetrate through the topsheet 38 where they are absorbed by the absorbent core 44. The topsheet 38 extends outwardly toward the edges of the absorbent core 44 so that a major portion of the absorbent core 44 is disposed between the backsheet 42 and the topsheet 38. In the preferred embodiment shown in FIG. 1, the topsheet 38 has length and width dimensions generally larger than those of the absorbent core 44. The topsheet 38 preferably extends longitudinally (i.e., lengthwise) beyond the waist edges 47 of the absorbent core 44 and is preferably longitudinally coterminous with the backsheet 42 to form the end edges 32 of the diaper 20. The topsheet 38 also preferably extends laterally (i.e. widthwise) toward the side edges 46 of the absorbent core 44, preferably beyond the side edges 46 in at least the crotch region 26, wherein the topsheet 38 terminates inwardly of the longitudinal edges 30, most preferably inwardly of the proximal edges 64 of the barrier cuffs 62. Inwardly is used herein to denote preferred configurations wherein the terminating edge of the topsheet 38 is positioned adjacent the proximal edge 64 (i.e., the topsheet 38 is substantially coterminous with the proximal edge 64) and configurations wherein the terminating edge of the topsheet 38 is positioned remotely from and inboard of the proximal edge 64. Adjacent is used in this context to mean that the topsheet terminates at the proximal edge, plus or minus small areas of topsheet material that may extend inside or beyond the proximal edges 64 due to machine tolerances during manufacture or variations in the topsheet's area when it is manufactured. In the most preferred embodiments as shown in FIG. 1, the topsheet 38 is positioned adjacent the proximal edge 64 and is secured to the gasketing flap 58 (backsheet 42) adjacent to the proximal edge 42 by the seal means 78 so as to form a leakage-resistant seal along the proximal edge 64.

The elastically contractible gasketing cuffs 56 are disposed adjacent the periphery 28 of the diaper 20, preferably adjacent each barrier cuff 62 along each longitudinal edge 30 so that the gasketing cuffs 56 tend to draw and hold the diaper 20 against the legs of the wearer. Alternatively, a gasketing cuff 56 may be disposed adjacent either or both of the end edges 32 of the diaper 20 to provide a waistcuff. While the gasketing cuffs 56 may comprise any of several means as are well known in the diaper art, a particularly preferred gasketing cuff construction comprises a flexible gasketing flap 58 and one or more flap elastic members 60, as is described in detail in the hereinbefore referenced U.S. Pat. No. 3,860,003 issued to K. B. Buell on Jan. 14, 1975, and which is herein incorporated by reference. In addition, a method and apparatus suitable for manfacturing a disposable diaper having elastically contractible gasketing cuffs 56 are described in U.S. Pat. No. 4,081,301 entitled "Method and Apparatus for Continuously Attaching Discrete, Stretched Elastic Strands to Predetermined Isolated Portions of Disposable Absorbent Articles" which issued to K. B. Buell on Mar. 28, 1978 and which patent is incorporated herein by reference. A particularly preferred waistcuff/gasketing cuff construction is described in U.S. Pat. No. 4,515,595 entitled "Disposable Diapers With Elastically Contractible Waistbands" which issued to D. J. Kievet and T. F. Osterhage on May 7, 1985 and which patent is incorporated herein by reference.

The gasketing flap 58 should be highly flexible and thus contractable so that the flap elastic members 60 may gather the gasketing flap 58 to provide a gasketing cuff 56 about the legs or waist of the wearer. The gasketing flaps 58 are that portion of the diaper 20 between the periphery 28 and the edges of the absorbent core 44. Thus in a preferred embodiment of the present invention as shown in FIG. 1, the gasketing flaps 58 are formed from the extension of the backsheet 42 and the flap portion 70 of the barrier cuffs 62 extending outwardly from and along the side edges 46 of the absorbent core 44 of the diaper 20 in at least the crotch region 26.

The flap elastic members 60 are operatively associated with the gasketing flaps 58 in an elastically contractible condition so that in a normally unrestrained configuration, the flap elastic members 60 effectively contract or gather the gasketing flaps 58. The flap elastic members 60 can be associated with the gasketing flaps 58 in an elastically contractible condition in at least two ways. For example, the flap elastic members 60 may be stretched and secured to the gasketing flaps 58 while the gasketing flaps 58 are in an uncontracted condition. Alternatively, the gasketing flaps 58 may be contracted, for example by pleating, and the flap elastic members 60 secured to the contracted gasketing flaps 58 while the flap elastic members 60 are in their unrelaxed or unstretched condition.

In the embodiment illustrated in FIG. 1, the flap elastic members 60 extend essentially the entire length of the gasketing flaps 58 in the crotch region 26 of the diaper 20. Alternatively, the flap elastic members 60 may extend the entire length of the diaper 20, or any other length suitable to provide an elastically contractible gasketing cuff. The length of the flap elastic members 60 is dictated by the diaper's design.

As shown in FIG. 2, the flap elastic members 60 are operatively associated with the gasketing flaps 58 by securing them to the gasketing flaps 58 with flap elastic attachments means 90. The flap elastic attachment means 90 should be flexible and of sufficient adhesiveness to hold the flap elastic member 60 in its stretched condition. The flap elastic attachment means 90 herein are preferably glue beads made of hot melt adhesives such as marketed by Findley Adhesives Incorporated, Elm Grove, Wis. as Findley Adhesives 581, although the flap elastic members 60 may be affixed to the diaper 20 in any of several other ways which are known in the art. For example, the flap elastic members 60 may be ultrasonically bonded or heat/pressure sealed into the diaper 20 using a variety of bonding patterns or the flap elastic members 60 may simply be glued to the diaper 20. A more detailed description of the manner in which the flap elastic members 60 may be positioned and secured to the diaper 20 can be found in U.S. Pat. No. 4,253,461 issued to Strickland and Visscher on Mar. 3, 1981, and U.S. Pat. No. 4,081,301 issued to Buell on Mar. 28, 1978, both of which are incorporated herein by reference.

One flap elastic member 60 which has been found to be suitable is an elastic strand having a cross section of 0.18 mm by 1.5 mm and made from natural rubber as available from Easthampton Rubber Thread Company of Stewart, Va., under the trademark L-1900 Rubber Compound. Other suitable flap elastic members 60 can be made from natural rubber, such as elastic tape sold under the trademark Fulflex 9411 by Fulflex Company of Middletown, R.I. The flap elastic member 60 may also comprise any heat shrinkable elastic material as is well known in the art. Other suitable flap elastic members 60 may comprise a wide variety of materials as are well known in the art including elastomeric films, polyurethane films, elastomeric foams, and formed elastic scrim.

In addition, the flap elastic members 60 may take a multitude of configurations. For example, the width of the flap elastic members 60 may be varied from about 0.25 mm (0.01 inches) to about 25 mm (1.0 inch) or more; the flap elastic members 60 may comprise a single strand of elastic material or may comprise several parallel or non-parallel strands of elastic material; or the flap elastic members 60 may be rectilinear or curvilinear.

The barrier cuffs 62 provide a barrier to restrain the free flow of body exudates along the liquid-receiving surface 40 and provide a structure to hold and contain such exudates within the diaper 20. Each barrier cuff 62 is a flexible member preferably having a flap portion 68 and a channel portion 70 comprising a proximal edge 64 and a distal edge 66. As used herein, the term "flexible" refers to materials which are compliant and will readily conform to the general shape and contours of the body. In addition, if the spacing means 76 comprises one or more spacing elastic members 77, the barrier cuffs 62 must be contractible so that the distal edges 66 may be sufficiently spaced away from the liquid-receiving surface 40 so that the channel 96 is open to constrain, retain and hold body exudates within the diaper 20. The barrier cuffs 62 may be manufactured from a wide variety of materials such as polypropylene, polyester, rayon, nylon, foams, plastic films, formed films, and elastic foams. A number of manufacturing techniques may be used to manufacture the barrier cuffs. For example, the barrier cuffs 62 may be woven, non-woven, spunbonded, carded, or the like. A particularly preferred barrier cuff 62 comprises a polypropylene material containing no finish or surfactant to render it liquid impermeable. A particularly preferred polypropylene material is manufactured by Crown Zellerbach Company as Celestra.

Referring to FIGS. 1 and 2, it can be seen that the barrier cuff 62 preferably has a flap portion 68 and a channel portion 70. The flap portion 68 is contiguous with the channel portion 70 and extends outwardly from the proximal edge 64 of the channel portion 70 toward the longitudinal edge 30, preferably to the longitudinal edge 30, such that the gasketing flap 58 is formed from the extension of the backsheet 42 and the flap portion 68.

While the flap portion 68 is preferably a continuous segment of the barrier cuff member, the flap portion 68 may be formed from a different piece of material secured to the channel portion 70 of the barrier cuff 62. Thus, the flap portion 68 may have different physical properties, dimensions, and characteristics than the channel portion 70. For example, the flap portion 68 need not be liquid impermeable nor extend outwardly to the longitudinal edge 30. In addition, each of the barrier cuffs 62 need not have a flap portion 68 such that a flap portion 68 may be omitted entirely. The flap portion 68 is, however, preferably hydrophobic, liquid impermeable, compliant, soft feeling and non-irritating to the wearer's skin since it contacts the legs of the wearer when in use.

The flap portion 68 of the barrier cuff 62 and the backsheet 42 are associated together in any suitable manner. As used herein, the term "associated" encompasses configuations whereby the flap portion 68 is directly joined to the backsheet 42 by affixing the flap portion 68 directly to the backsheet 42, and configurations whereby the flap portion 68 is indirectly joined to the backsheet 42 by affixing the flap portion 68 to intermediate members which in turn are affixed to the backsheet 42. In a preferred embodiment, the flap portion 68 and the backsheet 42 are joined directly to each other in the diaper periphery 28 adjacent and outboard of the proximal edges 64 by attachment means 88 such as an adhesive or any other atachment means such as heat/-pressure sealing, ultrasonic bonding of any other methods as are known in the art. For example, a uniform continuous layer of adhesive, a patterned layer of adhesive, or an array of separate lines or spots of adhesive may be used. The attachment means 88 are preferably a hot melt adhesive such as manufactured by Eastman Chemical Products Company of Kingsport, Tenn. and marketed under the tradename Eastobond A-3 or Century Adhesives, Inc. of Columbus, Ohio and marketed under the tradename Century 5227. (The distal attachment means 92 are also preferably the same type of means as the attachment means 88.) The liquid impermeable flap portion 68, the liquid impervious backsheet 42, and the attachment means 88 thus form a leakage-resistant seal along the edge of the diaper 20 to further enhance the containment characteristics of the diaper.

The channel portion 70 of the barrier cuff 62 comprises that portion of the barrier cuff 62 between the proximal edge 64 and the distal edge 66 and generally defines the channel 96 formed along the diaper 20. As shown in FIGS. 1 and 2, the channel portion 70 of the barrier cuff 62, and more particularly the proximal edge 64, is disposed adjacent to and preferably inboard of the gasketing cuff 56. The term "inboard" is defined as the direction toward the centerline (34 or 36, respectively) of the diaper 20 that is parallel to the respective edge of the diaper 20 along which the particular gasketing cuff 56 is disposed. The channel portion 70 of the barrier cuff 62, and more particularly the proximal edge 64, is preferably disposed inboard of the gasketing cuff 56, the flap elastic member 60, so that extrudates, especially loose fecal material which is not easily absorbed and tends to float along the liquid-receiving surface 40, will contact the channel portion 70 of the barrier cuff 62 and the channel 96 before it contact the gasketing cuff 56. The channel portion 70 of the barrier cuff 62 is disposed adjacent the gasketing cuff 56 to provide a more effective dual restraint against the flow of body exudates. The proximal edge 64 is preferably disposed between the flap elastic member 60 of the gasketing cuff 56 and the longitudinal centerline 36 of the diaper 20. Most preferably, the proximal edge 64 is disposed between the innermost flap elastic member 60 and the side edge 46 of the absorbent core 44 in at least the crotch region 26 of the diaper 20.

The proximal edges 64 and the distal edges 66 are in spaced relation to each other and define the effective width of the channel portion 70 of each of the barrier cuffs 62. The proximal and distal edges 64 and 66, respectively, may be in a parallel, nonparallel, rectilinear or curvilinear relationship. In addition, each of the barrier cuffs 62 may have a variety of different cross-sectional areas including circular, square, rectangular or any other shape such as that shown in FIGS. 2 and 3. Preferably, the proximal edge 64 is spaced from the distal edge 66 in a parallel and rectilinear relationship to provide a channel portion 70 having a uniform effective width. Each channel portion 70 preferably has an effective width of at least about 5 mm, and preferably from about 10 mm to about 50 mm.

The distal edge 66 is preferably disposed inboard of the proximal edge 64 to present a more effective barrier against the flow of exudates. The distal edges 66 are maintained inboard of the proximal edges 64 by the closing means 80 so as to obviate their inversion. While the distal edges 66 may alternatively be disposed in other positions in relation to the proximal edges 64, such positions are not preferred.

The distal edge 66 is preferably not secured to any underlying elements of the diaper 20 in at least the crotch region 26 so that it may be spaced away from the liquid-receiving surface 40. The distal edge 66 is preferably spaced away from the liquid-receiving surface 40 so that the channel portion 70 of the barrier cuff 62 may form a channel 96 to enhance the containment of the diaper 20. As used herein, "spaced" includes embodiments wherein the distal edges 66 may assume one or more positions relative to the liquid-receiving surface 40 including at some times assuming a position adjacent the liquid-receiving surface 40. The distance between the distal edge 66 to the liquid-receiving surface 40 is measured along a line drawn from the distal edge 66 to the closest part of the liquid-receiving surface 40 when the distal edge 66 is positioned so as to be spaced away from the liquid-receiving surface 40 as far as possible. (i.e., in the elastically contracted position). Preferably, the distal edge 66 is spaced away from the liquid-receiving surface 40 by a height of at least about 2 mm, and more preferably of at least from about 5 mm (about ¼") to about 10 mm (⅜").

A channel 96 is formed at least along the proximal and distal edges 64 and 66 and the inner surface of the channel portion 70 of the barrier cuff 62. The channel 96 forms a barrier to the flow of exudates as they tend to move or float across the topsheet 38. Thus, the channel 96 restains, contains and holds exudates within the diaper 20 until the diaper 20 can be removed.

The barrier cuffs 62 are preferably hydrophobic and more preferably liquid impermeable so as to prevent the strikethrough of body exudates. A liquid impermeable barrier cuff 62 retards the movement of liquid through the barrier cuff 62, thereby making it more leakage resistant. The barrier cuffs 62 may be rendered liquid impermeable in any manner well known in the art such as selectively treating the barrier cuffs, untreating the barrier cuffs, or by securing a separate material to the barrier cuffs.

The barrier cuffs 62 may additionally be provided with absorbent means secured to or within the barrier cuff 62. The absorbent means absorb and contain exudates which contact the barrier cuff 62. The absorbent means may be any means which is capable of absorbing and retaining liquids and may have any size, shape, configuration or absorbent capacity. The absorbent means may be positioned to the barrier cuff 62 along the inner surface of the channel portion 70 or within the barrier cuff 62. Preferably, the absorbent means is a layer of airfelt secured along the inner surface of the barrier cuff 62 and secured along the entire lengh and width of the inner surface of the channel portion 70.

A preferred embodiment of the diaper 20 shown in FIG. 1 is provided with each of the barrier cuffs 62 joined to the gasketing flaps 58 (i.e., the backsheet 42). The term "joined" includes any means for affixing the barrier cuff 62 to the diaper 20, and includes embodiments wherein the barrier cuffs 62 are separate members directly or indirectly secured to the gasketing flaps 58 (i.e., integral) or embodiments wherein the barrier cuffs 62 are constructed from the same member or material as an element of the diaper 20 such as the gasketing flap 58 (i.e., the backsheet 42) so that the barrier cuffs 62 are a continuous and undivided element of the gasketing flap 58 (i.e., unitary). The barrier cuffs 62 may alternatively be joined to the backsheet 42, the topsheet 38, the absorbent core 44, or any combination of these or other elements of the diaper 20. In the preferred embodiment, the barrier cuffs 62 are integral with the gasketing flaps 58. The integral barrier cuffs 62 are thus preferably formed by a single separate strip of material with an intermediate segment adjoined to the gasketing flap 58 by the seal means 78 such as adhesive to form the proximal edge 64, the distal edge 66 being formed by folding an end of the material back upon itself and being secured to another segment by the distal attachment means 92, and the remaining portion of the material, the flap portion 70, extending and terminating outboard of the proximal edge 64 and preferably associated with the backsheet 42 by attachment means 88 to define the gasketing flaps 58.

The proximal edges 64 and the gasketing flaps 58 (backsheet 42) are adjoined together in any suitable manner. As used herein, the term "adjoined" encompasses configurations whereby the proximal edges 64 are directly secured to the gasketing flaps 58 by affixing the proximal edges 64 directly to the backsheet 42, and configurations whereby the proximal edges 64 are indirectly secured to the gasketing flaps 58 by affixing the proximal edges 64 to intermediate members which in turn are affixed to the backsheet 42. In a preferred embodiment, the proximal edges 64 and the gasketing flaps 58 are directly secured to each other at least in the crotch region 26 by the seal means 78.

The seal means 78 of the present invention for adjoining the proximal edges 64 to the gasketing flaps 58 are shown in FIGS. 1, 2, and 3. The seal means 78 provide a leakage-resistant seal along the proximal edge 64 to present a barrier to the wicking of liquids through the topsheet 38 so as to prevent liquids from wicking underneath the barrier cuffs 62 to the edges of the diaper 20.

In a preferred embodiment as shown in FIGS. 1 and 2, the seal means 78 are positioned along the proximal edges, thus preferably inboard of the flap elastic members 60 in at least the crotch region 26 so that the topsheet 38 and preferably the absorbent core 44 do not extend beyond the seals means 78 in at least the crotch region 26 such that liquids may not wick past the seal means 78. While the topsheet 38 or the absorbent core 44 may extend beyond the seal means 78, protection against leakage of liquids emanating from the edges of the absorbent core 44 or wicking along the topsheet 38 is further provided by the leakage-resistant seal formed by the attachment means 88 which secure the liquid impervious backsheet 42 to the liquid impermeable flap portion 68 of the barrier cuffs 62. The seal means 78 may be any means for securing the proximal edges 64 to the gasketing flaps 58 such as heat/pressure sealing, ultrasonic bonding, or any other methods as are known in the art. The seal means 78 are preferably an adhesive bead consisting of hot melt adhesives such as the adhesives manufactured by Eastman Chemical Products Company of Kingsport, Tenn. and marketed under the tradename Eastobond A-3 or Century Adhesives, Inc. of Columbus, Ohio and marketed under the tradename Century 5227.

The spacing means 76 for spacing the distal edge 66 away from the liquid-receiving surface 40 is any member which gathers, contracts, stiffens, shortens or otherwise acts on the barrier cuff 62 so as to cause the barrier cuffs 62 to stand up to provide a channel 96 along the barrier cuff 62 that acts as a constraint against the leakage of exudates.

As shown in FIG. 1, the spacing means 76 preferably comprises a spacing elastic member 77 operatively associated with each of the barrier cuffs 62 adjacent the distal edge 66. The spacing elastic member 77 is preferably secured to the barrier cuff 62 in an elastically contractible condition so that in a normally unrestrained configuration, the spacing elastic member 77 effectively contracts or gathers the distal edge 66 of the barrier cuff 62. The spacing elastic member 77 can be secured to the barrier cuff 62 in an elastically contractible condition in at least two ways as is discussed in the above referenced U.S. Pat. No. 3,860,003 issued to K. B. Buell. In addition, the length of the spacing elastic member 77 in general is dictated by the diaper design. In the embodiment illustrated in FIG. 1, the spacing elastic member 77 extends essentially the entire length of the barrier cuff 36 in the crotch region 26, although other lengths are cognizable.

As shown in FIG. 2, the spacing elastic member 77 is operatively associated with the barrier cuff 62 by securing it within the barrier cuff 62 with a spacing elastic attachment means 94. The spacing elastic attachment means 94 should be flexible and of sufficient adhesiveness to hold the spacing elastic member 77 in its stretched condition. While the spacing elastic members 77 may be secured to the barrier cuff 62 adjacent only the ends of the spacing elastic member 77, it is preferable to secure the entire length of the spacing elastic member 77 to the barrier cuff 62. The spacing elastic attachment means 94 herein are preferably glue beads made of hot melt adhesive such as marketed by Findley Adhesives Incorporated, Elmgrove, Wis., as Findley Adhesies 581, although the spacing elastic members 77 may be affixed to the barrier cuff 62 in any of several other ways which are well known in the art. For example, the spacing elastic members 77 may be ultrasonically bonded or heat/pressure sealed into the barrier cuff 62 using a variety of bonding patterns, or the spacing elastic members 77 may simply be glued to the barrier cuffs 62. A more detailed description of the manner in which the spacing elastic members 77 may be positioned and secured to the barrier cuff 62 can be found in U.S. Pat. No. 4,081,301, issued to Buell on Mar. 28, 1978, and in U.S. Pat. No. 4,253,461, issued to Strickland and Visscher on Mar. 3, 1981, both of which are incorporated herein by reference. It should also be noted that one or more spacing elastic members 77 can be used to elasticize each barrier cuff 62.

A spacing elastic member 77 which has been found suitable is an elastic strand having a cross section of 0.18 mm by 1.5 mm and made from natural rubber as available from Easthampton Rubber Company of Stewart, Va., under the trademark L-1900 Rubber Compound. Other suitable spacing elastic members 77 can be made from natural rubber, such as elastic tape sold under the trademark Fulflex 9411 by Fulflex Company of Middletown, R.I. The spacing elastic member 77 may also comprise any heat shrinkable elastic material as is well known in the art. Other suitable elastic materials may comprise a wide variety of materials as are well known in the art include elastomeric films, polyurethane films, elastomeric foams and formed elastic scrim.

In addition, the spacing elastic members 77 may take a multitude of configurations. For example, the width of the spacing elastic members 77 may be varied; the spacing elastic members may comprise a single strand or several parallel or non-parallel strands of elastic material; or the spacing elastic members 77 may be rectilinear or curvilinear.

The spacing means 76 for spacing the distal edge 66 away from the liquid-receiving surface 40 may alternatively comprise several other elements. For example, the barrier cuff 62 may have stiffening means disposed in or on each barrier cuff 62. The stiffening means must be sufficiently stiff so that the distal edge 66 is spaced away from the liquid-receiving surface 40. Suitable materials for the stiffening means include foams, nonwoven fabrics, batting, polyethylene film, formed films, spray glues, foamed elastomerics, polyester, polyurethane, or a high loft material as is manufactured by Carolina Formed Fabrics.

The spacing means 76 may also comprise means for shortening the length of the distal edge 66 in comparison to the length of the edges of the diaper 20. The distal edge 66 can be shortened by making a fold or pleat in the distal edge 66. This fold or pleat is secured by any of the holding means well known to those of ordinary skill in the art, such as adhesives or heat sealing. Alternatively, a section may be cut out of the distal edge and the resultant edges brought together to form a butt or lapp joint. The distal edge 66 may also be shortened by attaching a length of the distal edge 66 to the topsheet 38 at a position different from where the distal edge 66 would lie when the diaper 20 is in a flattened out condition. Other shortening techniques as are known in the art may also be used.

The closing means 80 for securing the ends 72 of the barrier cuff 62 closed are shown in FIGS. 1 and 3. The closing means 80 provide a more comfortable fit for the wearer and obviate inversion of the distal edge 66 of the barrier cuff 62 during application and use. Inversion is generally defined as the inboard disposed distal edge 66 turning outwardly when the diaper 20 is applied to the wearer. In a preferred embodiment as shown in FIGS. 1 and 3, such closing means 80 are disposed in the front waist region 22 and the back waist region 24 of the diaper. The remaining portions of the barrier cuff 62 are not secured closed so that the distal edges 66 are left freely openable. In a preferred embodiment, the closing means 80 are positioned in the entire front waist region 22, while the closing means 80 are positioned in only a portion of the back waist region 24. This construction is preferred so as to create a channel 96 around the buttocks of the wearer to especially prevent leakage of loose fecal material.

While the closing means 80 may comprise any of several means as are known in the art such as ultrasonic bonding or heat/pressure sealing using a variety of bonding patterns or simple glues, the closing means 80 are preferably adhesive beads consisting of hot melt adhesives such as manufactured by Eastman Chemical Products Company of Kingsport, Tenn. and marketed under the tradename Eastobond A-3 or Century Adhesives, Inc. of Columbus, Ohio and marketed under the tradename Century 5227.

The diaper 20 is applied to a wearer by positioning the back waist region 24 under the wearer's back and drawing the remainder of the diaper 20 between the wearer's leg so that the front waist region 22 is positioned across the front of the wearer. The ends of the tape-tab fasteners 54 are then secured preferably to outwardly facing areas of the diaper 20. In this manner, the barrier cuffs 62 should be disposed in the crotch region of the wearer and should provide the dispositions and functions described hereinbefore. Once applied, the distal edges 66 of the barrier cuffs 62 extend through the groin areas and diverge upwardly along both of the buttocks of the wearer. Neither of the barrier cuffs 62 encircle the thighs of the wearer. However, the gasketing cuffs 56 will encircle the thighs and create a gasketing action against the thighs. The ends of the barrier cuff 62 are secured to the topsheet 38 to obviate the inversion of the barrier cuffs, for comfort for the wearer during application and use, and for ease of application.

Basically, without intending to limit the present invention, the present invention is a diaper that is especially useful and leakage resistant against loose fecal material and gushes of urine, the improved containment characteristics being achieved in the following manner. As such material is discharged onto the topsheet 38, some of the material flows or floats on the liquid-receiving surface 40 (hereinafter referred to as surface material) and some is absorbed by and wicks through the topsheet 38. The surface material moves from the point of discharge toward the longitudinal edges 30. Surface material will contact the barrier cuffs 62 along the channel portion 70. In normal use, the surface material will tend to collect in the channel 96 formed by the channel portion 70 of the barrier cuff 62; the material being held in the channels 96 until the diaper 20 can be removed. Improved containment is achieved because surface material would have to flow up the channel 96, which direction is substantially directly against the force of gravity when the wearer is in an upright position, in order to penetrate and flow over the distal edges 66 of the barrier cuffs 62. However, should such material flow or wick beyond the barrier cuffs 62, it is retarded from leaking out of the diaper 20 by the gasketing effect achieved by the gasketing cuffs 56, as they draw and gather the gasketing flaps 58 about the legs or waist of the wearer, thereby providing a second and independent effective barrier against leakage so as to further prevent the soiling of adjacent garments. Liquids that are absorbed by and wicked through the topsheet 38 migrate toward the edges of the diaper 20. Because the topsheet 38 terminates inwardly of the edges, and preferably inwardly of the proximal edges 64 of the barrier cuffs 62 and because a leakage-resistant seal is formed along the proximal edge 64, liquids will be generally prevented from wicking underneath and beyond the barrier cuffs 62 to the edges of the diaper.

An alternative embodiment of the present invention provides that the topsheet 38 may extend outwardly beyond the proximal edge 64 of the barrier cuff 62 while still providing protection against liquids wicking out of the edges of the diaper 20. The barrier cuff 62 has a flap portion 68 that is affixed to the backsheet 42 to form the gasketing flap 58 by the attachment means 88 adjacent the edge of the diaper 20 so as to provide a leakage-resistant seal along the edge of the diaper 20. The flap portion 68 is preferably liquid impermeable so as to provide the most effective leakage-resistant seal. The topsheet 38 may thus extend outwardly toward the edge of the diaper 20, beyond even the proximal edge 64 and/or the seal means 78, and need only terminate inwardly of the edge (i.e., the seal formed along the edge of the attachment means 88) of the diaper 20; liquids being thereby prevented from leaking or wicking from the edge of the diaper 20 due to the seal formed along the edge because the topsheet 38 is encased between the liquid impermeable flap portion 68 and the liquid impervious backsheet 42, and because the topsheet 38 terminates inwardly of the edge of the diaper 20.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A unitary disposable absorbent article comprising:
   an absorbent core have a garment surface and a body surface;
   a liquid impervious backsheet positioned adjacent said garment surface of said absorbent core;
   an elastically contractible gasketing cuff disposed adjacent to an edge of the absorbent article;
   a hydrophobic barrier cuff having a proximal edge and a distal edge, said barrier cuff disposed adjacent said gasketing cuff;
   spacing means operatively associated with said barrier cuffs for spacing said distal edge away from the liquid-receivig surface of the absorbent article so as to cause said barrier cuff to stand up;
   seal means positioned along said proximal edge for adjoining said proximal edge to the absorbent article so as to provide a leakage-resistant seal along said proximal edge; and
   a liquid pervious topsheet positioned adjacent said body surface of said absorbent core, said topsheet extending outwardly toward and terminating inwardly of said proximal edge,
   whereby liquids are generally prevented from wicking underneath and beyond said barrier cuff to the edge of the absorbent article.

2. The absorbent article of claim 1 wherein said topsheet is positioned adjacent said proximal edge.

3. The absorbent article of claim 1 wherein said barrier cuff is liquid impermeable.

4. A unitary disposable absorbent article comprising:
   an absorbent core having edges, a garment surface and a body surface;
   a liquid impervious backsheet positioned adjacent said garment surface of said absorbent core;
   a gasketing flap extending outwardly from and along each of a pair of oppositely disposed edges of said absorbent core;
   a flap elastic member operatively associated with each of said gasketing flaps to thereby form gasketing cuffs;
   a hydrophobic barrier cuff positioned adjacent each of said gasketing cuffs, said barrier cuff having a channel portion comprising a proximal edge and a distal edge;
   spacing means operatively associated with said barrier cuff for spacing said distal edge away from the liquid-receiving surface of the absorbent article so as to cause said barrier cuff to stand up;
   seal means positioned along said proximal edge for adjoining said proximal edge to said gasketing flap so as to provide a leakage-resistant seal along said proximal edge; and
   a liquid pervious topsheet positioned adjacent said body surface of said absorbent core, said topsheet extending outwardly toward and terminating inwardly of said proximal edge,
   whereby liquids are generally prevented from wicking underneath and beyond said barrier cuff to the edges of the absorbent article.

5. The absorbent article of claim 4 wherein said topsheet is positioned adjacent said proximal edge and is secured to said gasketing flap by said seal means.

6. The absorbent article of claim 4 wherein said barrier cuff additionally comprises a flap portion contiguous with said channel portion, said flap portion extending outwardly from said proximal edge toward the edge of the absorbent article.

7. The absorbent article of claim 4 wherein said proximal edge is disposed inboard of said flap elastic member.

8. The absorbent article of claim 4 wherein at least said channel portion of said barrier cuff is liquid impermeable.

9. The absorbent article of claim 4 wherein said barrier cuff is integral with said gasketing flap.

10. A unitary disposable absorbent article having a front waist region, a back waist region, and a crotch region, said absorbent article comprising:
    an absorbent core having side edges, a garment surface, and a body surface;
    a liquid impervious backsheet positioned adjacent said garment surface of said absorbent core;
    a gasketing flap extending outwardly from and along each side edge of said absorbent core in at least the crotch region;
    a flap elastic member operatively associated with each of said gasketing flaps to thereby form gasketing cuffs;
    a hydrophobic barrier cuff disposed adjacent each of said gasketing cuffs, said barrier cuffs each having a channel portion comprising a proximal edge and a distal edge, each of said proximal edges being positioned inboard of said flap elastic member in at least the crotch region;
    spacing means operatively associated with said barrier cuff for spacing said distal edge away from the liquid-receiving surface of the absorbent article so as to cause said barrier cuff to stand up;

seal means positioned along each of said proximal edges for adjoining each of said proximal edges to said gasketing flaps so as to provide a leakage-resistant seal along said proximal edges; and a liquid pervious topsheet positioned adjacent said body surface of said absorbent core, said topsheet extending outwardly toward and terminating inwardly of each of said proximal edges, wherby liquids are generally prevented from wicking underneath and beyond said barrier cuff to the edges of the absorbent article.

11. The absorbent article of claim 10 wherein said spacing means comprises a spacing elastic member.

12. The absorbent article of claim 11 wherein said backsheet extends beyond each of said side edges of said absorbent core to form said gasketing flaps.

13. The absorbent article of claim 12 wherein each of said barrier cuffs additionally comprises a flap portion contiguous with said channel portion, said flap portion extending outwardly from said proximal edge toward the longitudinal edges of the absorbent article such that said gasketing flaps are formed from the extension of said backsheet and said flap portions.

14. The absorbent article of claim 13 wherein at least said channel portion of said barrier cuffs is liquid impermeable.

15. The absorbent article of claim 14 wherein said barrier cuffs are integral with said gasketing flaps.

16. The absorbent article of claim 15 wherein said topsheet is positioned adjacent each of said proximal edges and is secured to said gasketing flaps by said seal means.

17. A unitary disposable absorbent article comprising:
an absorbent core having a garment surface and a body surface;

a liquid impervious backsheet positioned adjacent said garment surface of said absorbent core;

an elastically contractible gasketing cuff disposed adjacent to a pair of oppositely disposed edges of the absorbent article, each of said gasketing cuffs comprising a gasketing flap and a flap elastic member;

a hydrophobic barrier cuff having a flap portion and a channel portion comprising a proximal edge and a distal edge, said barrier cuff disposed adjacent said gasketing cuff;

spacing means operatively associated with said barrier cuff for spacing said distal edge away from the liquid-receiving surface of the absorbent article so as to cause said barrier cuff to stand up;

attachment means positioned adjacent the edge of the absorbent article for associating said flap portion of said barrier cuff with said gasketing flap so as to provide a leakage-resistant seal along the edge of the absorbent article; and a liquid pervious topsheet positioned adjacent said body surface of said absorbent core, said topsheet extending outwardly toward and terminating inwardly of the oppositely disposed pair of edges of the absorbent article, whereby liquids are generally prevented from wicking beyond the edges of the absorbent article.

18. The absorbent article of claim 17 additionally comprising a seal means positioned along said proximal edge for adjoining said proximal edge to said gasketing flap.

19. The absorbent article of claim 18 wherein said barrier cuff is integral with said gasketing flaps.

20. The absorbent article of claim 19 wherein said proximal edge is disposed inboard of said flap elastic member.

21. The absorbent article of claim 19 wherein said flap portion is liquid impermeable.

* * * * *

UNITED STATES PATENT AND TRADEMARK OFFICE
CERTIFICATE OF CORRECTION

PATENT NO. : 4,795,454

DATED : January 3, 1989

INVENTOR(S) : Jerry L. Dragoo

It is certified that error appears in the above-identified patent and that said Letters Patent is hereby corrected as shown below:

| | |
|---|---|
| Column 4, Line 34, | "completelt" should read ---completely---. |
| Column 12, Line 2, | "it contact" should read ---it can contact---. |
| Column 13, Line 18, | "lengh" should read ---length---. |
| Column 14, Line 65, | "Adhesies" should read ---Adhesives---. |
| Column 17, Line 54, in Claim 1 | "receivig" should read ---receiving---. |

Signed and Sealed this

Sixth Day of June, 1989

Attest:

DONALD J. QUIGG

Attesting Officer

Commissioner of Patents and Trademarks

(12) REEXAMINATION CERTIFICATE (4379th)
United States Patent
Dragoo (10) Number: US 4,795,454 C1
(45) Certificate Issued: Jun. 26, 2001

(54) ABSORBENT ARTICLE HAVING LEAKAGE RESISTANT DUAL CUFFS

(75) Inventor: Jerry L. Dragoo, Fairfield, OH (US)

(73) Assignee: The Procter & Gamble Company, Cincinnati, OH (US)

Reexamination Request:
No. 90/005,476, Sep. 7, 1999

Reexamination Certificate for:
Patent No.: 4,795,454
Issued: Jan. 3, 1989
Appl. No.: 07/117,379
Filed: Oct. 30, 1987

Certificate of Correction issued Jun. 6, 1989.

Related U.S. Application Data (63) Continuation of application No. 06/917,450, filed on Oct. 10, 1986, now abandoned.

(51) Int. Cl.$^7$ .................................................. A61F 13/15
(52) U.S. Cl. ..................................... 604/385.28; 604/378
(58) Field of Search ............................ 604/385.01, 378, 604/385.28

(56) References Cited

U.S. PATENT DOCUMENTS

| | | |
|---|---|---|
| Re. 26,151 | 1/1967 | Duncan et al. . |
| Re. 33,106 | 11/1989 | Beckestrom . |
| Re. 34,920 | 4/1995 | Aziz et al. . |
| 2,545,674 | 3/1951 | Ralph . |
| 2,575,164 | 11/1951 | Donovan . |
| 2,714,889 | 8/1955 | Chambers . |
| 2,745,405 | 5/1956 | Landy et al. . |
| 2,862,251 | 12/1958 | Kalwaites . |
| 2,893,393 | 7/1959 | Pressley . |
| 2,916,037 | 12/1959 | Hansen . |
| 3,081,514 | 3/1963 | Griswold . |
| 3,081,515 | 3/1963 | Griswold . |
| 3,364,931 | 1/1968 | Hirsch . |
| 3,386,442 | 6/1968 | Sabee . |
| 3,452,753 | 7/1969 | Sanford . |

(List continued on next page.)

FOREIGN PATENT DOCUMENTS

| | | |
|---|---|---|
| 188667 | 2/1957 | (AT) . |
| 45217/85 | 2/1986 | (AU) . |
| 1070779 | 12/1959 | (DE) . |
| 0027303 | 4/1981 | (EP) . |
| 0070584 | 1/1983 | (EP) . |
| 0070584A1 | 1/1983 | (EP) . |
| 0091412 | 10/1983 | (EP) . |

(List continued on next page.)

OTHER PUBLICATIONS

The Wall Street Journal, Apr. 5, 1999.

*Primary Examiner*—Dennis Ruhl (57) ABSTRACT

An integral disposable absorbent article such as a diaper provided with an absorbent core, a liquid impervious backsheet, an elastically contractible gasketing cuff preferably formed by a gasketing flap and a flap elastic member, a barrier cuff having a flap portion and a channel portion comprising a proximal edge and a distal edge, and a liquid pervious topsheet. The topsheet extends outwardly toward the edge of the absorbent core and terminates inwardly of the proximal edge. A seal means for adjoining the proximal edge to the gasketing flap is positioned along the proximal edge so as to provide a leakage-resistant seal along the proximal edge. The barrier cuffs may be provided with spacing means for spacing the distal edges away from the liquid-receiving surface so as to enhance the containment characteristics of the barrier cuffs. Thus, body exudates which wick through and along the topsheet are prevented from flowing to the edges of the diaper and underneath the barrier cuffs because of the seal formed along the proximal edges and because the topsheet terminates inwardly of the proximal edges.

U.S. PATENT DOCUMENTS

| | | |
|---|---|---|
| 3,485,706 | 12/1969 | Evans . |
| 3,530,859 | 9/1970 | Helmowitz . |
| 3,561,446 | 2/1971 | Jones, Sr. . |
| 3,570,493 | 3/1971 | Olsson . |
| 3,572,342 | 3/1971 | Lindquist et al. . |
| 3,593,716 | 7/1971 | Vogt . |
| 3,612,055 | 10/1971 | Mesek et al. . |
| 3,658,063 | 4/1972 | Schaar . |
| 3,658,064 | 4/1972 | Pociluyko . |
| 3,663,348 | 5/1972 | Liloia et al. . |
| 3,665,920 | 5/1972 | Davis . |
| 3,667,466 | 6/1972 | Ralph . |
| 3,744,494 | 7/1973 | Marsan . |
| 3,759,261 | 9/1973 | Wang . |
| 3,769,978 | 11/1973 | DeNight et al. . |
| 3,771,524 | 11/1973 | Ralph . |
| 3,807,402 | 4/1974 | Miller et al. . |
| 3,825,006 | 7/1974 | Ralph . |
| 3,828,784 | 8/1974 | Zoephel . |
| 3,848,594 | 11/1974 | Buell . |
| 3,848,598 | 11/1974 | Mesek . |
| 3,860,002 | 1/1975 | Kolbach . |
| 3,860,003 | 1/1975 | Buell . |
| 3,885,568 | 5/1975 | Schaar . |
| 3,886,941 | 6/1975 | Duane et al. . |
| 3,900,031 | 8/1975 | Endres et al. . |
| 3,906,952 | 9/1975 | Zamist . |
| 3,913,578 | 10/1975 | Schaar . |
| 3,920,017 | 11/1975 | Karami . |
| 3,929,134 | 12/1975 | Karami . |
| 3,930,501 | 1/1976 | Schaar . |
| 3,943,930 | 3/1976 | Schaar . |
| 3,965,906 | 6/1976 | Karami . |
| 3,978,861 | 9/1976 | Schaar . |
| 3,995,640 | 12/1976 | Schaar . |
| 3,999,547 | 12/1976 | Hernandez . |
| 3,999,548 | 12/1976 | Hernandez . |
| 4,040,423 | 8/1977 | Jones, Sr. . |
| 4,041,950 | 8/1977 | Jones, Sr. . |
| 4,041,951 | 8/1977 | Sanford . |
| 4,044,769 | 8/1977 | Papajohn . |
| 4,050,462 | 9/1977 | Woon et al. . |
| 4,081,301 | 3/1978 | Buell . |
| 4,090,515 | 5/1978 | Karami . |
| 4,094,319 | 6/1978 | Joa . |
| 4,108,179 | 8/1978 | Schaar . |
| 4,173,612 | 11/1979 | Kelly . |
| 4,210,143 | 7/1980 | De Jonckheere . |
| 4,246,900 | 1/1981 | Schröder . |
| 4,253,461 | 3/1981 | Strickland et al. . |
| 4,259,958 | 4/1981 | Goodbar . |
| 4,305,990 | 12/1981 | Kelly . |
| 4,319,572 | 3/1982 | Widlund et al. . |
| 4,326,528 | 4/1982 | Ryan et al. . |
| 4,333,782 | 6/1982 | Pieniak . |
| 4,337,771 | 7/1982 | Pieniak et al. . |
| 4,341,216 | 7/1982 | Obenour . |
| 4,352,355 | 10/1982 | Mesek et al. . |
| 4,381,782 | 5/1983 | Mazurak et al. . |
| 4,395,215 | 7/1983 | Bishop . |
| 4,397,645 | 8/1983 | Buell . |
| 4,402,688 | 9/1983 | Julemont . |
| 4,402,690 | 9/1983 | Redfern . |
| 4,413,996 | 11/1983 | Taylor . |
| 4,425,127 | 1/1984 | Suzuki et al. . |
| 4,430,086 | 2/1984 | Repke . |
| 4,437,860 | 3/1984 | Sigl et al. . |
| 4,490,148 | 12/1984 | Beckeström . |
| 4,496,360 | 1/1985 | Joffe et al. . |
| 4,500,316 | 2/1985 | Damico . |
| 4,527,989 | 7/1985 | Karami . |
| 4,578,073 | 3/1986 | Dysart et al. . |
| 4,579,556 | 4/1986 | McFarland . |
| 4,589,876 | 5/1986 | Van Tilburg . |
| 4,591,523 | 5/1986 | Thompson . |
| 4,597,760 | 7/1986 | Buell . |
| 4,597,761 | 7/1986 | Buell . |
| 4,601,717 | 7/1986 | Blevins . |
| 4,623,342 | 11/1986 | Ito . |
| 4,636,207 | 1/1987 | Buell . |
| 4,650,483 | 3/1987 | Joffe . |
| 4,657,539 | 4/1987 | Hasse . |
| 4,662,877 | 5/1987 | Williams . |
| 4,681,579 | 7/1987 | Toussant et al. . |
| 4,687,478 | 8/1987 | Van Tilburg . |
| 4,695,278 | 9/1987 | Lawson . |
| 4,704,115 | 11/1987 | Buell . |
| 4,704,116 | 11/1987 | Enloe . |
| 4,738,677 | 4/1988 | Foreman . |
| 4,743,246 | 5/1988 | Lawson . |
| 4,747,991 | 5/1988 | Bishop . |
| 4,753,646 | 6/1988 | Enloe . |
| 4,795,454 | 1/1989 | Dragoo .............................. 604/385.2 |
| 4,808,178 | 2/1989 | Aziz et al. . |
| 4,816,025 | 3/1989 | Foreman . |
| 4,846,823 | 7/1989 | Enloe . |
| 4,900,317 | 2/1990 | Buell . |
| 4,909,803 | 3/1990 | Aziz et al. . |
| 4,938,755 | 7/1990 | Foreman . |
| 5,085,654 | 2/1992 | Buell . |
| 5,413,570 | 5/1995 | Enloe . |
| 5,415,644 | 5/1995 | Enloe . |
| 5,599,338 | 2/1997 | Enloe . |
| B1 4,636,207 | 11/1989 | Buell . |

FOREIGN PATENT DOCUMENTS

| | | |
|---|---|---|
| 2063794 | 7/1971 | (FR) . |
| 2561078 A1 | 9/1985 | (FR) . |
| 358765 | 10/1931 | (GB) . |
| 667483 | 3/1952 | (GB) . |
| 790062 | 2/1958 | (GB) . |
| 1543915 | 4/1979 | (GB) . |
| 2063677A | 6/1981 | (GB) . |
| 2101468A | 1/1983 | (GB) . |
| 2130491A | 6/1984 | (GB) . |
| 2149289A | 6/1985 | (GB) . |
| 2159693A | 12/1985 | (GB) . |
| 2161059A | 1/1986 | (GB) . |
| 2193625A | 2/1988 | (GB) . |
| 33-9632 | 7/1958 | (JP) . |
| 36-7548 | 4/1961 | (JP) . |
| 39-33810 | 11/1964 | (JP) . |
| 39-33813 | 11/1964 | (JP) . |
| 40-1548 | 1/1965 | (JP) . |
| 40-11543 | 4/1965 | (JP) . |
| 40-21930 | 7/1965 | (JP) . |
| 41-17377 | 8/1966 | (JP) . |
| 41-18031 | 8/1966 | (JP) . |
| 41-18359 | 8/1966 | (JP) . |
| 42-7943 | 4/1967 | (JP) . |
| 42-11718 | 6/1967 | (JP) . |
| 52-40267 | 10/1977 | (JP) . |
| 54-10050 | 1/1979 | (JP) . |
| 57-89602 | 6/1982 | (JP) . |
| 58-105405 | 7/1983 | (JP) . |
| 59-25741 | 2/1984 | (JP) . |
| 59-28508 | 2/1984 | (JP) . |
| 59-76903 | 5/1984 | (JP) . |
| 59-146651 | 8/1984 | (JP) . |
| 60-104502 | 6/1985 | (JP) . |
| 196521 | 6/1983 | (NZ) . |

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–21 is confirmed.

* * * * *